(12) United States Patent
Dodda et al.

(10) Patent No.: US 9,469,628 B2
(45) Date of Patent: Oct. 18, 2016

(54) PROCESSES FOR THE PREPARATION OF HIGHLY PURE RIVAROXABAN CRYSTAL MODIFICATION I

(71) Applicant: SYMED LABS LIMITED, Banjara Hills, Hyderabad (IN)

(72) Inventors: Mohan Rao Dodda, Telangana (IN); Venugopal Bingi, Huzurabad (IN)

(73) Assignee: Symed Labs Limited (IN)

( * ) Notice: Subject to any disclaimer, the term of this patent is extended or adjusted under 35 U.S.C. 154(b) by 67 days.

(21) Appl. No.: 14/601,419

(22) Filed: Jan. 21, 2015

(65) Prior Publication Data

US 2015/0203482 A1 Jul. 23, 2015

(30) Foreign Application Priority Data

Jan. 23, 2014 (IN) .............................. 290/CHE/2014

(51) Int. Cl.
 C07D 413/14 (2006.01)

(52) U.S. Cl.
 CPC .................................. C07D 413/14 (2013.01)

(58) Field of Classification Search
 None
 See application file for complete search history.

(56) References Cited

U.S. PATENT DOCUMENTS

| | | | |
|---|---|---|---|
| 7,351,823 B2 | 4/2008 | Berwe et al. | |
| 7,585,860 B2 | 9/2009 | Straub et al. | |
| 7,816,355 B1 | 10/2010 | Bodhuri et al. | |
| 8,188,270 B2 | 5/2012 | Grunenberg et al. | |
| 2011/0152266 A1 | 6/2011 | Grunenberg et al. | |

FOREIGN PATENT DOCUMENTS

| | | |
|---|---|---|
| WO | 2009149851 A1 | 12/2009 |
| WO | 2010075631 A1 | 7/2010 |
| WO | 2011012321 A1 | 3/2011 |
| WO | 2011080341 A1 | 7/2011 |
| WO | 2011098501 A1 | 8/2011 |
| WO | 2012004245 A1 | 1/2012 |
| WO | 2012032533 A1 | 3/2012 |
| WO | 2012156983 A1 | 11/2012 |
| WO | 2013027225 A1 | 2/2013 |
| WO | 2013046211 A1 | 4/2013 |
| WO | 2013105100 A1 | 7/2013 |
| WO | 2013118130 A1 | 8/2013 |
| WO | 2013121436 A2 | 8/2013 |
| WO | 2013164833 A1 | 11/2013 |
| WO | 2015111076 A2 | 7/2015 |
| WO | 2015111076 A3 | 7/2015 |

OTHER PUBLICATIONS

International Search Report and Written Opinion of PCT/IN2015/000031 dated Jul. 13, 2015.

Roehrig, et al., Discovery of the Novel Antithrombotic Agent 5-Chloro-N-(5S)-2-oxo-3-[4-(3-oxomorpholin-4-yl)phenyl]-1,3-oxazolidin-5-yl]methyl)thiophene-2-carboxamide (BAY 59-7939): An Oral, Direct Factor Xa Inhibitor J. Med. Chem. 2005, 48, 5900-5908.

*Primary Examiner* — Samantha Shterengarts (74) *Attorney, Agent, or Firm* — Caesar Rivise, PC (57) ABSTRACT

Provided herein are improved, commercially viable and consistently reproducible processes for the preparation of highly pure crystal Modification I of Rivaroxaban, which is free from other polymorphs and undesired solvated forms. Provided also herein is a highly pure and stable crystal Modification I of Rivaroxaban essentially free of other solid state forms.

24 Claims, 3 Drawing Sheets

Figure 1: Powder X-ray diffraction (XRPD) pattern of Crystal Modification I of Rivaroxaban Figure 2: Infra-red (IR) spectrum of Crystal Modification I of Rivaroxaban Figure 3: Differential Scanning Calorimetric (DSC) thermogram of Crystal Modification I of Rivaroxaban

PROCESSES FOR THE PREPARATION OF HIGHLY PURE RIVAROXABAN CRYSTAL MODIFICATION I

CROSS REFERENCE TO RELATED APPLICATION

This patent application claims the benefit of priority to Indian Complete Patent Application No. 290/CHE/2014 filed on Jan. 23, 2014, which is incorporated herein by reference in its entirety.

FIELD OF THE INVENTION

The present invention relates to improved, commercially viable and industrially advantageous processes for the preparation of highly pure crystal Modification I of Rivaroxaban, which is free from other polymorphs and undesired solvated forms.

BACKGROUND OF THE INVENTION

U.S. Pat. No. 7,585,860 discloses a variety of substituted oxazolidinone derivatives and their salts, processes for their preparation, pharmaceutical compositions comprising the derivatives, and methods of use thereof. These compounds are anticoagulants which inhibit the blood coagulation factor Xa with increased selectivity. Among them, Rivaroxaban, 5-chloro-N-[[(5S)-2-oxo-3-[4-(3-oxomorpholin-4-yl)phenyl]oxazolidin-5-yl]methyl]thiophene-2-carboxamide, acts as inhibitor of clotting factor Xa and which is used as agent for the prophylaxis and/or treatment of thromboembolic disorders, in particular myocardial infarction, angina pectoris, reocclusions and restenoses after angioplasty or aortocoronary bypass, stroke, transient ischaemic attacks, peripheral arterial occlusive diseases, pulmonary embolisms or deep venous thromboses. Rivaroxaban is represented by the following structural formula I:

I

Rivaroxaban is sold by Bayer under the brand name Xarelto® and it is orally administered as tablets containing 10 mg of Rivaroxaban.

Various processes for the preparation of Rivaroxaban and its intermediates are apparently disclosed in U.S. Pat. Nos. 7,585,860; 7,351,823 and 7,816,355; PCT Publication Nos. WO 2011/012321, WO 2011/080341, WO 2011/098501, WO 2012/032533, WO 2012/156983, WO 2013/027225, WO 2013/046211, WO 2013/105100, WO 2013/118130 and WO 2013/164833; and J. Med. Chem. 2005, 48, 5900-5908.

According to U.S. Pat. No. 7,585,860 (hereinafter referred to as the U.S. '860 patent), Rivaroxaban is prepared by reacting 4-[4-[(5S)-5-(aminomethyl)-2-oxo-1,3-oxazolidin-3-yl]phenyl]morpholine-3-one of formula (II) with thiophene carboxylic acid of the formula (III) or else with a corresponding carbonyl halide, or else with a corresponding symmetric or mixed carboxylic anhydride of the carboxylic acid of the formula (III) in an inert solvent, if appropriate in the presence of an activating or coupling agent and/or a base.

As per the process exemplified in example 44 of the '860 patent, Rivaroxaban is prepared by drop-wise addition of 5-chlorothiophene-2-carbonyl chloride to a solution of 4-[4-[(5S)-5-(aminomethyl)-2-oxo-1,3-oxazolidin-3-yl]phenyl]morpholine-3-one in pyridine at 0° C. under argon, followed by removal of ice-cooling and stirring the reaction mixture at room temperature for 1 hour and then admixing with water. After addition of dichloromethane and phase separation, the aqueous phase was extracted with dichloromethane. The combined organic phases were dried, filtered, and evaporated in vacuo. The residue was purified by Flash chromatography (dichloromethane/methanol mixtures) to produce Rivaroxaban.

According to the PCT Publication No. WO 2013/164833 (hereinafter referred to as the WO '833 publication), Rivaroxaban is prepared by reacting 5-Chlorothiophene-2-carboxylic acid with a sulfonylating agent (e.g., methanesulfonyl chloride or p-toluenesulfonyl chloride) in the presence of a base such as 1-Methylimidazole in dichloromethane to produce a reaction mass containing a corresponding sulfonyl ester intermediate, followed by condensation with (S)-4-[4-[5-(Aminomethyl)-2-oxo-oxazolidin-3-yl]phenyl]morpholin-3-one to produce Rivaroxaban.

Rivaroxaban is known to exhibit polymorphism and various solid state forms including crystalline modifications (I, II & III), amorphous form, hydrate form, dihydrate form, solvated forms and co-crystals of rivaroxaban are apparently disclosed in U.S. Pat. No. 8,188,270; and PCT Publication Nos. WO 2009/149851, WO 2010/075631 and WO 2012/004245.

U.S. Pat. No. 8,188,270 (hereinafter referred to as the U.S. '270 patent), assigned to Bayer Schering Pharma, discloses three crystalline modifications (modifications I, II & III) and four solid state forms (an amorphous form, a hydrate, an NMP solvate and an inclusion compound with THF) of Rivaroxaban, processes for their preparation, and characterizes the modifications and the solid state forms by powder X-ray diffraction (XRPD), Infra Red spectrum (IR), Raman spectrum, Far Infra Red spectrum (FIR), Near Infra Red spectrum (NIR) and Differential Scanning Calorimetric thermogram (DSC).

The U.S. '270 patent teaches that when Rivaroxaban was originally produced, for example, as per the process described in the U.S. '860 patent, the crystal form was crystal modification I (hereinafter referred to as the Crystalline Form I), which is characterized by having melting point of 230° C.; a powder X-ray diffraction spectrum having peaks expressed as 2-theta angle positions at 8.9, 12.0, 14.3, 16.5, 17.4, 18.1, 19.5, 19.9, 21.7, 22.5, 23.4, 24.1, 24.5, 24.7, 25.6, 26.4, 26.7, 30.0, 30.1 and 31.8 degrees; and an IR spectrum having bands at 564, 686, 708, 746, 757, 830, 846, 920, 991, 1011, 1056, 1077, 1120, 1146, 1163, 1219, 1286, 1307, 1323, 1341, 1374, 1411, 1429, 1470, 1486, 1517, 1546, 1605, 1646, 1669, 1737, 2867, 2895, 2936, 2976 and 3354 cm$^{-1}$.

The U.S. '270 patent neither discloses nor teaches any processes (except the process described in the U.S. '860 patent) for the preparation of crystal Modification I of Rivaroxaban. However, the processes for preparation of the crystal Modification I of Rivaroxaban as described in the aforementioned prior art suffer from several disadvantages such as lack of reproducibility; contamination of the desired crystal Modification I with other solid state forms and solvated forms; require the use of column chromatographic purifications; the use of excess amounts of solvents which generate a large quantity of chemical waste which is difficult to treat. The main drawback of the processes for the preparation of Rivaroxaban as described in the U.S. '860 patent is that the crystal Modification I of Rivaroxaban obtained by the process described therein does not have satisfactory purity (e.g., about 92% purity by HPLC) and which is found to be contaminated with other polymorphic forms and solvated forms.

Based on the aforementioned drawbacks, the crystal Modification I of Rivaroxaban obtained according to the prior art processes is an impure form and therefore not suitable for pharmaceutical formulations and therapeutic use thereof.

A need still remains for simple, cost effective, consistently reproducible and environmentally friendly processes for preparing highly pure crystal Modification I of Rivaroxaban which is free from other polymorphs and solvated forms.

SUMMARY OF THE INVENTION

Extensive research and experimentation was carried out by the present inventors to produce highly pure Rivaroxaban in crystal Modification I essentially free from other polymorphic forms and solvated/hydrated forms. As a result, the present inventors have surprisingly and unexpectedly found that highly pure crystal Modification I of Rivaroxaban essentially free of other polymorphic forms and solvated/hydrated forms, can be obtained in an improved, efficient and cost effective process by providing a solution of Rivaroxaban in a solvent medium comprising water and acetone at reflux, subjecting the solution to carbon treatment, cooling the solution to below about room temperature to cause crystallization, and then collecting the highly pure crystal Modification I of Rivaroxaban.

Provided herein are simple, commercially viable, consistently reproducible and environmentally friendly processes for the preparation of highly pure crystal Modification I of Rivaroxaban essentially free from other solid state forms such as crystalline forms, amorphous form and solvated and/or hydrated forms.

Surprisingly, the processes disclosed herein advantageously produce the crystal Modification I of Rivaroxaban with high chemical and enantiomeric purity (Chemical purity: greater than about 99.95% by HPLC and Enantiomeric purity: 99.999% by HPLC).

In another aspect, provided herein is a highly pure crystal Modification I of Rivaroxaban essentially free of other solid state forms of Rivaroxaban.

In another aspect, provided herein is a pharmaceutical composition comprising highly pure crystal Modification I of Rivaroxaban essentially free of other solid state forms made by the processes disclosed herein, and one or more pharmaceutically acceptable excipients.

In still further aspect, encompassed herein is a process for preparing a pharmaceutical formulation comprising combining highly pure crystal Modification I of Rivaroxaban essentially free of other solid state forms made by the processes disclosed herein with one or more pharmaceutically acceptable excipients.

In another aspect, the highly pure crystal Modification I of Rivaroxaban essentially free of other solid state forms, made by the processes disclosed herein for use in the pharmaceutical compositions, has a $D_{90}$ particle size of less than or equal to about 200 microns, specifically about 1 micron to about 100 microns, and most specifically about 4 microns to about 80 microns.

The processes for the preparation of crystal Modification I of Rivaroxaban described herein has the following advantages over the processes described in the prior art:
i) the processes consistently produces the crystal Modification I of Rivaroxaban with high purity which is essentially free of other solid state forms;
ii) the processes avoid the use of expensive column chromatographic purifications;
iii) the processes involves easy work-up methods and simple isolation/crystallization techniques, and there is a reduction in chemical waste.

DETAILED DESCRIPTION OF THE INVENTION

According to one aspect, there is provided a process for the preparation of Crystal Modification I of Rivaroxaban, comprising:
a) providing a solution of Rivaroxaban in a solvent medium comprising water and acetone at an ambient temperature;
b) optionally, subjecting the solution obtained in step-(a) to carbon treatment to obtain a filtrate;
c) cooling the solution obtained in step-(a) or step-(b) at a temperature of below about 35° C. to cause crystallization; and
d) recovering the highly pure crystal Modification I of Rivaroxaban formed in step-(c).

The use of the specific solvent medium comprising water and acetone employed herein for crystallization of Rivaroxaban surprisingly and unexpectedly allows the product (Modification I of Rivaroxaban) to be easily isolated and purified, thereby producing a product with high chemical, enantiomeric and polymorphic purity.

Usually, the amount of solvent medium employed in step-(a) is about 20 volumes to about 100 volumes, specifically about 35 volumes to about 80 volumes, with respect to the quantity of Rivaroxaban used.

In one embodiment, the amount of acetone employed in step-(a) is about 1 to 5 volumes, specifically about 3 to 4 volumes, with respect to the volume of water used.

Step-(a) of providing a solution of Rivaroxaban includes dissolving or extracting either an impure (or crude) form or a pure form of Rivaroxaban in the solvent medium comprising water and acetone, or obtaining an existing solution from a previous processing step.

In one embodiment, the Rivaroxaban is dissolved or extracted in the solvent medium comprising water and acetone at a temperature of about 40° C. to the reflux temperature of the solvent medium used, specifically at a temperature of about 50° C. to the reflux temperature, and more specifically at the reflux temperature. After complete dissolution of Rivaroxaban, the resulting solution is stirred at the reflux temperature for at least 5 minutes, and specifically for about 10 minutes to about 20 minutes.

Alternatively, the solution in step-(a) is also prepared by suspending Rivaroxaban in the solvent medium comprising water and acetone at room temperature, followed by heating the suspension at a temperature of about 40° C. to the reflux temperature to form a clear solution, specifically at the reflux temperature of the solvent medium used. After complete dissolution of Rivaroxaban, the resulting solution is stirred at the reflux temperature for at least 5 minutes, and specifically for about 10 minutes to about 20 minutes.

Alternatively, the solution in step-(a) is prepared by reacting 4-[4-[(5S)-5-(aminomethyl)-2-oxo-1,3-oxazolidin-3-yl]phenyl]morpholine-3-one with 5-Chlorothiophene-2-carboxylic acid (or else with a corresponding carbonyl halide or a corresponding sulfonyl ester derivative, or else with a corresponding symmetric or mixed carboxylic anhydride), optionally in the presence of a base, in an inert solvent to produce a reaction mass containing Rivaroxaban, followed by usual work up such as washings, extractions, evaporations or a combination thereof, and then dissolving or extracting the resulting Rivaroxaban in the solvent medium comprising water and acetone at a temperature of about 45° C. to the reflux temperature, specifically at a temperature of about 50° C. to the reflux temperature, and most specifically at the reflux temperature.

The carbon treatment in step-(b) is carried out by methods known in the art, for example, by stirring the solution with finely powdered carbon at a temperature of about 45° C. to the reflux temperature for at least 5 minutes, specifically at the reflux temperature; and filtering the resulting mixture through charcoal bed to obtain a filtrate containing Rivaroxaban by removing charcoal. Specifically, finely powdered carbon is a special carbon or an active carbon.

In one embodiment, the crystallization in step-(c) is accomplished by cooling the solution at a temperature of about 0° C. to about 35° C. for at least 10 minutes, and more specifically at a temperature of about 20° C. to about 30° C. for about 15 minutes to about 2 hours.

The recovering in step-(d) is carried out by the methods such as filtration, filtration under vacuum, decantation, centrifugation or a combination thereof.

According to another aspect, there is provided a process for the preparation of Crystal Modification I of Rivaroxaban, comprising:
a) providing a solution of Rivaroxaban in acetone or a solvent medium comprising water and acetone at an ambient temperature;
b) optionally, subjecting the solution obtained in step-(a) to carbon treatment to obtain a filtrate;
c) combining the solution obtained in step-(a) or step-(b) with water to cause crystallization; and
d) recovering the highly pure crystal Modification I of Rivaroxaban formed in step-(c).

Usually, the amount of solvent medium employed in step-(a) is about 20 volumes to about 100 volumes, specifically about 35 volumes to about 80 volumes, with respect to the quantity of Rivaroxaban used.

In one embodiment, the amount of acetone in the solvent medium employed in step-(a) is about 1 to 5 volumes, specifically about 3 to 4 volumes, with respect to the volume of water used.

The solution in step-(a) is prepared by the methods as described hereinabove.

The carbon treatment or silica gel treatment in step-(b) is carried out by the methods as described hereinabove.

Combining of the solution with water in step-(c) is done in a suitable order, for example, the solution of Rivaroxaban is added to the water, or alternatively, the water is added to the solution. The addition is, for example, carried out drop wise or in one portion or in more than one portion. The addition is specifically carried out under stirring at a temperature of about 20° C. to the reflux temperature of the solvent medium used, and most specifically at about 25° C. to about 45° C., to cause crystallization. After completion of the addition process, the resulting mass is stirred at a temperature of below 35° C. for at least 10 minutes and specifically at a temperature of about 20° C. to about 30° C. for about 20 minutes to about 5 hours.

The recovering in step-(d) is carried out by the methods such as filtration, filtration under vacuum, decantation, centrifugation or a combination thereof.

According to another aspect, there is provided a process for the preparation of Crystal Modification I of Rivaroxaban, comprising:
a) providing a suspension of Rivaroxaban in a solvent medium comprising water and acetone;
b) heating the suspension formed in step-(a) at a temperature of about 50° C. to the reflux temperature of the solvent medium used for sufficient time to obtain Crystal Modification I of Rivaroxaban;
c) cooling the hot suspension to below about 35° C.; and
d) recovering the highly pure crystal Modification I of Rivaroxaban formed in step-(c).

Usually, the amount of solvent medium employed in step-(a) is about 5 volumes to about 40 volumes, specifically about 25 volumes to about 35 volumes, with respect to the quantity of Rivaroxaban used.

In one embodiment, the amount of acetone employed in step-(a) is about 1 to 5 volumes, specifically about 3 to 4 volumes, with respect to the volume of water used.

Step-(a) of providing a suspension of Rivaroxaban includes suspending Rivaroxaban in the solvent medium comprising water and acetone, or obtaining an existing suspension from a previous processing step.

In one embodiment, the suspension in step-(b) is heated at the reflux temperature of the solvent medium used while stifling for at least 30 minutes, and most specifically for about 1 hour to about 10 hours.

In another embodiment, the suspension in step-(c) is cooled while stirring at a temperature of about 0° C. to about 30° C. for at least 10 minutes, and more specifically at a temperature of about 20° C. to about 30° C. for about 15 minutes to about 2 hours.

The recovering in step-(d) is carried out by the methods such as filtration, filtration under vacuum, decantation, centrifugation or a combination thereof.

As used herein, the term "reflux temperature" means the temperature at which the solvent or solvent system refluxes or boils at atmospheric pressure.

As used herein, the term "ambient temperature" is intended to mean the temperature at which the Rivaroxaban is completely dissolved in acetone or the solvent medium comprising water and acetone to provide a clear solution.

As used herein, the term "room temperature" or "RT" refer to a temperature of about 15° C. to about 35° C. For example, "RT" can refer to a temperature of about 20° C. to about 30° C.

The term "Rivaroxaban Modification I", otherwise called "Crystalline Form I of Rivaroxaban" or "Rivaroxaban Form I", as used herein is intended to mean the crystal Modification I of Rivaroxaban as designated in the U.S. Pat. No. 8,188,270 patent.

Figure 1:
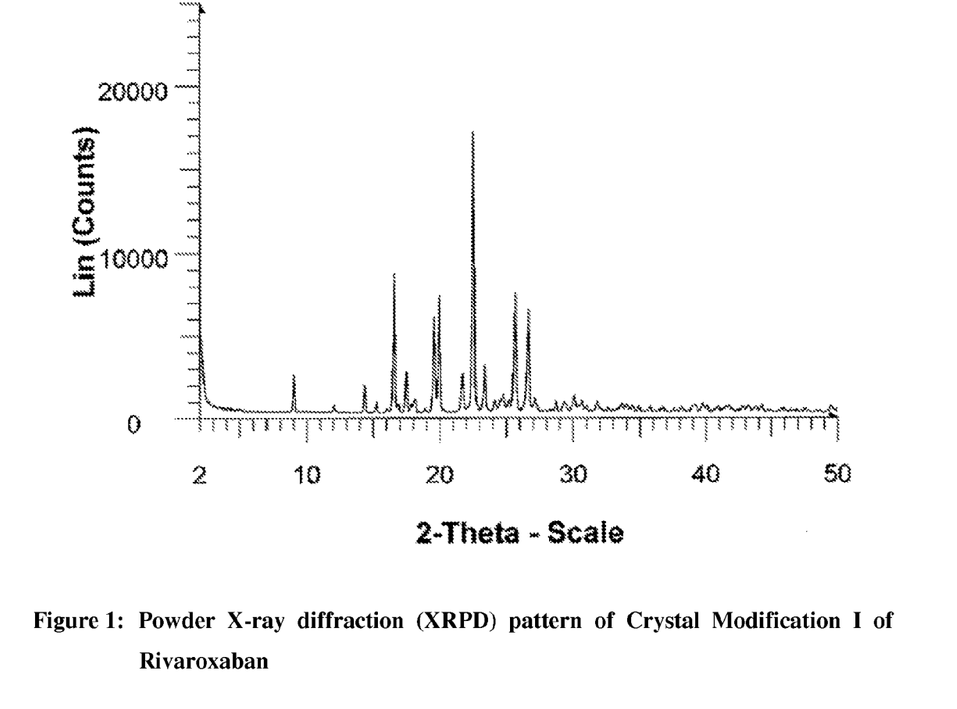
FIG. 1 is a characteristic powder X-ray diffraction (XRPD) pattern of Crystal Modification I of Rivaroxaban.
Figure 2:
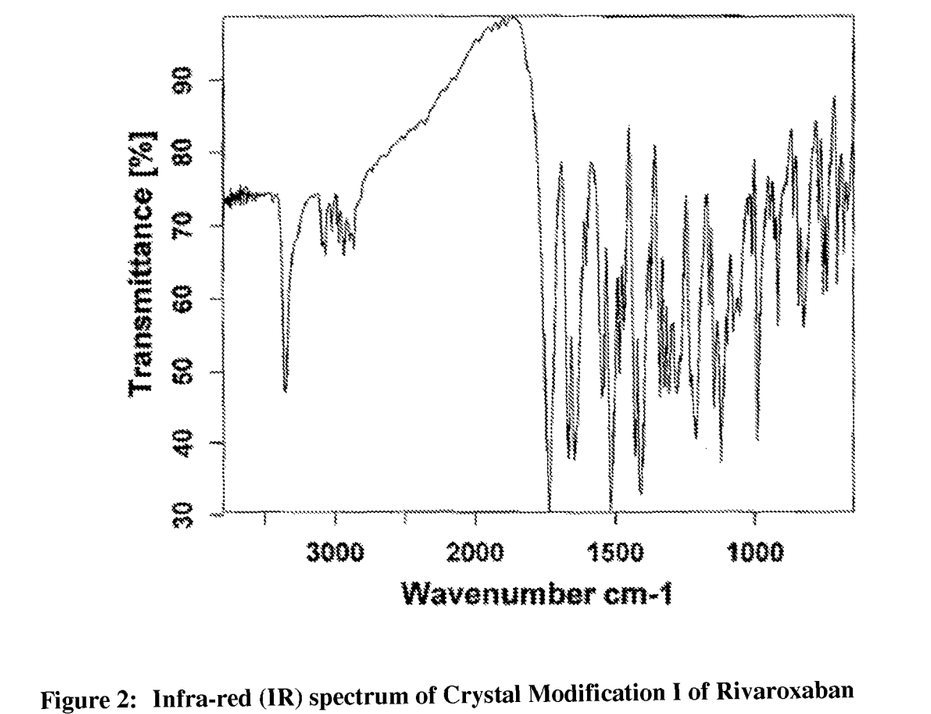
FIG. 2 is a characteristic infra-red (IR) spectrum of Crystal Modification I of Rivaroxaban.
Figure 3:
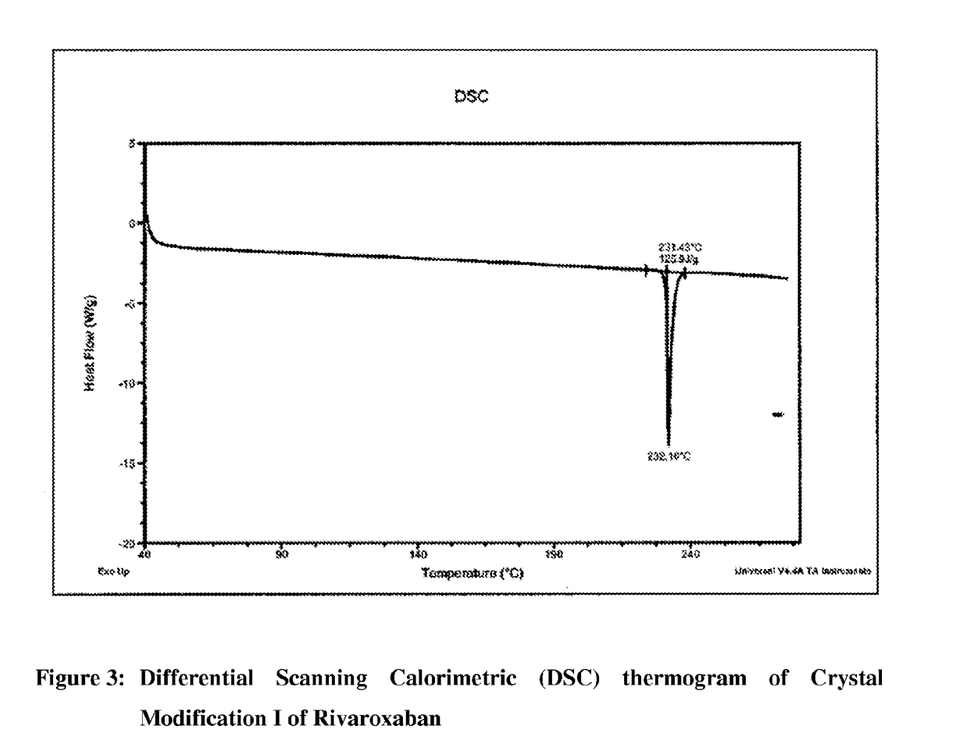
FIG. 3 is a characteristic Differential Scanning Calorimetric (DSC) thermogram of Crystal Modification I of Rivaroxaban.

In one embodiment, the crystal Modification I of Rivaroxaban obtained by the process disclosed herein is characterized by an X-ray powder diffraction pattern having peaks expressed as 2-theta angle positions at about 9.0, 12.0, 14.3, 16.5, 17.4, 18.1, 19.5, 19.9, 21.7, 22.5, 23.4, 24.1, 24.5, 24.7, 25.6, 26.6, 30.1 and 31.8±0.2 degrees substantially in accordance with FIG. 1; an infra red (FT-IR) spectrum having main bands at about 685, 707, 745, 756, 846, 919, 991, 1010, 1055, 1077, 1120, 1145, 1163, 1285, 1307, 1323, 1340, 1374, 1408, 1429, 1469, 1486, 1517, 1546, 1605, 1647, 1669, 1736, 2867, 2896, 2936, 2976 and 3353 cm$^{-1}$±2 substantially in accordance with FIG. 2; and a Differential Scanning Calorimetric (DSC) thermogram having a sharp endotherm peak at about 232° C. substantially in accordance with FIG. 3.

In one embodiment, the crystal Modification I of Rivaroxaban obtained by the processes disclosed herein is essentially free from other solid state forms of Rivaroxaban detectable by the spectral methods typically used, e.g., Powder X-ray diffraction.

The term "crystal Modification I of Rivaroxaban essentially free of other solid state forms" means that no other solid state forms of Rivaroxaban can be detected within the limits of a powder X-ray diffractometer. The term "other solid state forms of Rivaroxaban" is intended to mean the solid state forms of Rivaroxaban other than Modification I, including crystalline forms, amorphous form, solvated forms, hydrated forms and mixtures thereof.

Surprisingly, the processes disclosed herein above advantageously produces the crystal Modification I of Rivaroxaban with high chemical, enantiomeric and polymorphic purity.

The highly pure Rivaroxaban crystal Modification I obtained by the processes disclosed herein has a total purity (including both chemical and enantiomeric purities) of greater than about 99.8%, specifically greater than about 99.9%, more specifically greater than about 99.95%, and most specifically greater than about 99.98% as measured by HPLC. For example, the chemical purity of the highly pure Rivaroxaban crystal Modification I obtained by the processes disclosed herein is about 99.9% to about 99.99% as measured by HPLC, and the enantiomeric purity is greater than about 99.99% as measured by HPLC.

Unless otherwise specified, the term "crude or impure form of Rivaroxaban" refers to any form of Rivaroxaban having purity less than about 99.8%, preferably less than about 98%, and more preferably less than about 92% as measured by HPLC.

The highly pure Rivaroxaban crystal Modification I obtained by the above processes may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

Preferably, the drying is carried out at atmospheric pressure at temperatures such as about 35° C. to about 80° C. and most preferably at about 70° C. to about 75° C. In one embodiment, the drying is carried out for any desired time period that achieves the desired result, preferably shorter periods of time such as about 1 to 8 hours and more preferably about 2 to 4 hours. Drying can be suitably carried out in a tray dryer, a vacuum oven, an air oven, or using a fluidized bed drier, a spin flash dryer, a flash dryer and the like. Drying equipment selection is well within the ordinary skill in the art.

Unless otherwise specified, the Rivaroxaban as used herein as starting material can be obtained by the processes described in the prior art, for example, as per the processes described in the U.S. Pat. No. 7,585,860 and PCT Publication No. WO 2013/164833.

The highly pure Rivaroxaban crystal Modification I obtained by the processes disclosed herein is free from other solid state forms and solvated forms, which has very good flow properties and is consistently reproducible, and is found to be more stable. The Rivaroxaban crystal Modification I obtained by the processes disclosed herein exhibits properties making it suitable for formulating Rivaroxaban.

Further encompassed herein is the use of the highly pure Rivaroxaban crystal Modification I essentially free of other solid state forms, made by the processes disclosed herein, for the manufacture of a pharmaceutical composition together with a pharmaceutically acceptable carrier.

A specific pharmaceutical composition of Rivaroxaban crystal Modification I essentially free of other solid state forms is selected from a solid dosage form and an oral suspension.

In one embodiment, the Rivaroxaban crystal Modification I essentially free of other solid state forms made by the processes disclosed herein, for use in the pharmaceutical compositions, has a $D_{90}$ particle size of less than or equal to about 200 microns, specifically about 1 microns to about 100 microns, and most specifically about 4 microns to about 80 microns.

In another embodiment, the particle sizes of the highly pure Rivaroxaban crystal Modification I are accomplished by a mechanical process of reducing the size of particles which includes any one or more of cutting, chipping, crushing, milling, grinding, micronizing, trituration or other particle size reduction methods known in the art, to bring the solid state form to the desired particle size range.

The term "micronization" used herein means a process or method by which the size of a population of particles is reduced.

As used herein, the term "micron" or "µm" both are equivalent and refer to "micrometer" which is $1\times10^{-6}$ meter.

As used herein, "crystalline particles" means any combination of single crystals, aggregates and agglomerates.

As used herein, "Particle Size Distribution (P.S.D)" means the cumulative volume size distribution of equivalent spherical diameters as determined by laser diffraction in Malvern Master Sizer 2000 equipment or its equivalent.

The important characteristics of the PSD is the $D_{90}$ or D(0.90), which is the size, in microns, below which 90% of the particles by volume are found, and the $D_{50}$, which is the size, in microns, below which 50% of the particles by volume are found. Thus, a $D_{90}$ or D(0.90) of less than 100 microns means that 90 volume-percent of the particles in a composition have a diameter of less than 100 microns.

According to another aspect, there are provided pharmaceutical compositions comprising highly pure Rivaroxaban crystal Modification I essentially free of other solid state forms prepared according to the processes disclosed herein and one or more pharmaceutically acceptable excipients.

According to another aspect, there is provided a process for preparing a pharmaceutical formulation comprising combining highly pure Rivaroxaban crystal Modification I essentially free of other solid state forms, prepared according to processes disclosed herein, with one or more pharmaceutically acceptable excipients.

Yet in another embodiment, pharmaceutical compositions comprise at least a therapeutically effective amount of highly pure Rivaroxaban crystal Modification I essentially free of other solid state forms made by the process disclosed herein. Such pharmaceutical compositions may be administered to a mammalian patient in a dosage form, e.g., solid, liquid, powder, elixir, aerosol, syrups, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. The highly pure Rivaroxaban crystal Modification I essentially free of other solid state forms made by the processes disclosed herein may also be administered as suppositories, ophthalmic ointments and suspensions, and parenteral suspensions, which are administered by other routes.

The pharmaceutical compositions further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinbelow.

Other excipients include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Instrumental Details:
X-Ray Powder Diffraction (P-XRD):

The X-ray powder diffraction spectrum was measured on a BRUKER AXS D8 FOCUS X-ray powder diffractometer equipped with a Cu-anode (copper-K$\alpha$ radiation). Approximately 1 gm of sample was gently flattered on a sample holder and scanned from 2 to 50 degrees 2-theta, at 0.03 degrees to theta per step and a step time of 38 seconds. The sample was simply placed on the sample holder. The sample was rotated at 30 rpm at a voltage 40 KV and current 35 mA.

Infra-Red Spectroscopy (FT-IR):

FT-IR spectroscopy was carried out with a Bruker vertex 70 spectrometer. For the production of the KBr compacts approximately 5 mg of sample was powdered with 200 mg of KBr. The spectra were recorded in transmission mode ranging from 3800 cm$^{-1}$ to 650 cm$^{-1}$.

Differential Scanning Calorimetry (DSC):

Differential Scanning calorimetry (DSC) measurements were performed with a Differential Scanning calorimeter (DSC Q200 V23.10 Build 79, Universal V4.4A TA Instruments) equilibrated at 40° C. and Ramp at a scan rate of 10° C. per minute to 280° C.

Particle Size Method of Analysis (PSD):

Particle Size Distribution (PSD) is determined by laser diffraction in a Malvern Mastersizer 2000 (Ver. 5.22) equipment or its equivalent under the following conditions: Accessory Name=Hydro 2000S; Dispersant=Water; Dispersant Refractive Index=1.33; Absorption=0.1; Obscuration limit=5% to 20%; Measurement time=10 seconds; Measurement snaps=1000; Background time=10 seconds; Background snaps=10000; Pump/Stir speed=2000 RPM.

HPLC Method for Measuring Chemical Purity:

The chemical purity was measured by HPLC using Shimadzu LC-2010 CHT system with UV detector or its equivalent under the following conditions: Column=Zorbax SB-CN, 250 mm×4.6 mm, 5 μm or Equivalent; Detector wavelength=250 nm; Flow Rate=1.0 ml/minute; Injection volume=10 μL; Oven temperature=35° C.; Run time=65 minutes; Diluent=Water:Acetonitrile (60:40 v/v); Elution=Gradient; and Sample Concentration: 0.5 mg/ml.

Mobile Phase-A: 4 g of tetra n-butyl ammonium Hydrogen sulphate+6 g of monobasic sodium phosphate+2000 mL water, pH was adjusted to 2.40 with dilute orthophosphoric acid (50% v/v).

Mobile Phase-B: Methanol.

HPLC Method for Measuring Chiral Purity:

The chiral purity was measured by HPLC using Shimadzu LC-2010 CHT system with UV detector or its equivalent under the following conditions: Column=CHIRALPAK IC, 250 mm×4.6 mm, 5 μm or Equivalent; Detector wavelength=270 nm; Sample Concentration: 1.0 mg/ml; Run time=30 minutes; Oven temperature: 25° C.; Diluent=Methanol: Acetonitrile (50:50 v/v); Elution=Isocratic; Flow Rate: 1.0 ml/minute; Injection Volume: 10 μL; Mobile Phase=Acetonitrile (980 ml): Methanol (20 ml): diethyl amine (1.0 ml).

The following examples are given for the purpose of illustrating the present invention and should not be considered as limitation on the scope or spirit of the invention.

EXAMPLES

Example 1

Preparation of Pure Crystal Modification I of Rivaroxaban

Acetone (1740 ml) and water (540 ml) were added to crude Rivaroxaban (30 g, Purity by HPLC: 91.95%) at 25-30° C. and the contents were stirred for 5 to 10 minutes at the same temperature, followed by heating the resulting mixture at reflux temperature (about 56° C.) to form a clear solution. Carbon powder (3 g) was added to the resulting solution at reflux and then stirred for 5 minutes at the same temperature. The reaction mixture was filtered through charcoal bed and then washed the bed with acetone (10 ml). The resulting filtrate was cooled to 25-30° C., followed by stirring the mass for 30 minutes at the same temperature. The separated solid was filtered, washed the solid two times with water (50 ml) and then dried the material at 80-85° C. for 3 to 4 hours to produce 24 g of pure crystal Modification I of Rivaroxaban (Purity by HPLC: 99.95%; Enantiomeric Purity by HPLC: 99.999%; Particle Size Data: D(0.90)=45.30 microns and D(0.50)=17.57 microns).

Example 2

Rivaroxaban Modification I (obtained from example 1) was fine-milled by being passed through a grinder (Make: Morphy Richards, Model-Icon DLX) having stainless steel liquidizing blade for 3-4 minutes to obtain 90 volume-% (i.e., $D_{90}$) of the particles of Rivaroxaban Modification I having a diameter of less than or equal to about 5 microns.

Example 3

Acetone (290 ml) and water (90 ml) were added to crude Rivaroxaban (5 g, Purity by HPLC: 98%) at 25-30° C. and the contents were stirred for 5 to 10 minutes at the same temperature, followed by heating the resulting mixture at reflux temperature (about 56° C.) for 10 to 15 minutes to form a clear solution. Carbon powder (0.5 g) was added to the resulting solution at reflux and then stirred for 10 minutes at the same temperature. The reaction mixture was filtered through charcoal bed and then washed the bed with hot acetone (10 ml). The resulting filtrate was cooled to 25-30° C., followed by the addition of water (200 ml) while stirring at the same temperature. The resulting mass was stirred for 30 minutes at 25-30° C. The separated solid was filtered, washed the solid two times with water (40 ml) and then dried the material at 80-85° C. for 3 to 4 hours to produce 4.25 g of pure crystal Modification I of Rivaroxaban (Purity by HPLC: 99.90%; Enantiomeric Purity by HPLC: 99.90%).

Example 4

Acetone (114.5 ml) and water (35.5 ml) were added to Rivaroxaban (5 g, Purity by HPLC: 98%) at 25-30° C. and the contents were stirred for 5 to 10 minutes at the same temperature, followed by heating the resulting mixture at reflux temperature (about 56° C.) for 1 hour to form a hot suspension. The resulting suspension was cooled to 25-30° C., followed by stirring the mass for 30 minutes at the same temperature. The separated solid was filtered, washed the solid two times with water (40 ml) and then dried the material at 80-85° C. for 3 to 4 hours to produce 4.50 g of pure crystal Modification I of Rivaroxaban (Purity by HPLC: 99.90%; Enantiomeric Purity by HPLC: 99.90%).

Unless otherwise indicated, the following definitions are set forth to illustrate and define the meaning and scope of the various terms used to describe the invention herein.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host, e.g., human, animal, etc.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dihydrate and other such materials known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia, alginic acid, tragacanth, carboxymethylcellulose sodium, polyvinylpyrrolidone, compressible sugar, ethylcellulose, gelatin, liquid glucose, methylcellulose, pregelatinized starch, starch, polyethylene glycol, guar gum, polysaccharide, bentonites, sugars, invert sugars, poloxamers, collagen, albumin, celluloses in non-aqueous solvents, polypropylene glycol, polyoxyethylene-polypropylene copolymer, polyethylene ester, polyethylene sorbitan ester, polyethylene oxide, microcrystalline cellulose, combinations thereof and other material known to those of ordinary skill in the art.

The term "diluents" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pregelatinized, sweeteners, clays, such as bentonite, microcrystalline cellulose, carsium, alginates, sodium starch glycolate, gums such as agar, guar, locust bean, karaya, pectin, tragacanth, combinations thereof and other such materials known to those of ordinary skill in the art. The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxylpropylcellulose, hydroxypropylmethylcellulose phthalate, noncrystalline cellulose, magnesium aluminum silicate, triethanolamine, polyvinyl alcohol, and polyvinylpyrrolidone (PVP).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A process for the preparation of Crystal Modification I of Rivaroxaban, comprising:
   a) providing a solution of Rivaroxaban in a solvent medium comprising water and acetone at an ambient temperature;
   b) optionally, subjecting the solution obtained in step-(a) to carbon treatment to obtain a filtrate;
   c) cooling the solution obtained in step-(a) or step-(b) at a temperature of below about 35° C. to cause crystallization; and
   d) recovering highly pure crystal Modification I of Rivaroxaban formed in step-(c).

2. The process of claim 1, wherein the amount of solvent medium employed in step-(a) is about 35 volumes to about 80 volumes with respect to the quantity of Rivaroxaban used; wherein the amount of acetone employed in the solvent medium in step-(a) is about 1 to 5 volumes with respect to the volume of water used; and wherein the solution in step-(a) is prepared by dissolving or extracting Rivaroxaban in the solvent medium comprising water and acetone at a temperature of about 50° C. to the reflux temperature of the solvent medium used.

3. The process of claim 2, wherein the amount of acetone employed in the solvent medium is about 3 to 4 volumes with respect to the volume of water used; and wherein the solution in step-(a) is prepared by dissolving or extracting Rivaroxaban in the solvent medium comprising water and acetone at the reflux temperature of the solvent used.

4. The process of claim 1, wherein the solution in step-(a) is prepared by reacting 4-[4-[(5S)-5-(aminomethyl)-2-oxo-1,3-oxazolidin-3-yl]phenyl]morpholine-3-one with 5-Chlorothiophene-2-carboxylic acid, or with a corresponding carbonyl halide or a corresponding sulfonyl ester derivative, or with a corresponding symmetric or mixed carboxylic anhydride, optionally in the presence of a base, in an inert solvent to produce a reaction mass containing Rivaroxaban, followed by washings, extractions, evaporations or a combination thereof, and then dissolving or extracting the resulting Rivaroxaban in the solvent medium comprising water and acetone at a temperature of about 45° C. to the reflux temperature of the solvent medium used.

5. The process of claim 1, wherein the carbon treatment in step-(b) is carried out stirring the solution with finely powdered carbon at a temperature of about 45° C. to the reflux temperature for at least 5 minutes, followed by filtering the resulting mixture through charcoal bed to obtain a filtrate containing Rivaroxaban; wherein the crystallization in step-(c) is accomplished by cooling the solution at a temperature of about 15° C. to about 35° C. for at least 10 minutes; and wherein the recovering in step-(d) is carried out by filtration, filtration under vacuum, decantation, centrifugation or a combination thereof.

6. The process of claim 5, wherein the carbon treatment in step-(b) is carried out stirring the solution with finely powdered carbon at the reflux temperature; and wherein the crystallization in step-(c) is accomplished by cooling the solution at a temperature of about 20° C. to about 30° C. for about 15 minutes to about 20 hours.

7. The process of claim 1, wherein the highly pure Rivaroxaban crystal Modification I obtained has chemical purity of greater than about 99.9% as measured by HPLC and enantiomeric purity of greater than about 99.99% as measured by HPLC; and wherein crystal Modification I of Rivaroxaban obtained is essentially free from other solid state forms of Rivaroxaban.

8. The process of claim 1, wherein the crystal Modification I of Rivaroxaban obtained is characterized by an X-ray powder diffraction pattern having peaks expressed as 2-theta angle positions at about 9.0, 12.0, 14.3, 16.5, 17.4, 18.1, 19.5, 19.9, 21.7, 22.5, 23.4, 24.1, 24.5, 24.7, 25.6, 26.6, 30.1 and 31.8±0.2 degrees substantially in accordance with FIG. 1; and an infra red (FT-IR) spectrum having main bands at about 685, 707, 745, 756, 846, 919, 991, 1010, 1055, 1077, 1120, 1145, 1163, 1285, 1307, 1323, 1340, 1374, 1408, 1429, 1469, 1486, 1517, 1546, 1605, 1647, 1669, 1736, 2867, 2896, 2936, 2976 and 3353 cm$^{-1}$±2 substantially in accordance with FIG. 2.

9. A process for the preparation of Crystal Modification I of Rivaroxaban, comprising:
   a) providing a solution of Rivaroxaban in acetone or a solvent medium comprising water and acetone at an ambient temperature;
   b) optionally, subjecting the solution obtained in step-(a) to carbon treatment to obtain a filtrate;
   c) combining the solution obtained in step-(a) or step-(b) with water to cause crystallization; and
   d) recovering the highly pure crystal Modification I of Rivaroxaban formed in step-(c).

10. The process of claim 9, wherein the amount of solvent medium employed in step-(a) is about 35 volumes to about 80 volumes with respect to the quantity of Rivaroxaban used; wherein the amount of acetone employed in the solvent medium in step-(a) is about 1 to 5 volumes with respect to the volume of water used; and wherein the solution in step-(a) is prepared by dissolving or extracting Rivaroxaban in acetone or in the solvent medium comprising water and acetone at a temperature of about 50° C. to the reflux temperature of the solvent medium used.

11. The process of claim 10, wherein the amount of acetone employed in the solvent medium is about 3 to 4 volumes with respect to the volume of water used; and wherein the solution in step-(a) is prepared by dissolving or extracting Rivaroxaban in acetone or in the solvent medium comprising water and acetone at the reflux temperature of the solvent/solvent medium used.

12. The process of claim 9, wherein the combining in step-(c) is accomplished by adding the solution of Rivaroxaban to water or by adding water to the solution of Rivaroxaban, wherein the addition is carried out under stirring at a temperature of about 20° C. to the reflux temperature of the solvent medium used to cause crystallization; and wherein the recovering in step-(d) is carried out by filtration, filtration under vacuum, decantation, centrifugation or a combination thereof.

13. The process of claim 12, wherein the addition is carried out under stirring at a temperature of about 25° C. to about 45° C. and wherein the resulting mass is stirred at a temperature of about 20° C. to about 30° C.

14. The process of claim 9, wherein the highly pure Rivaroxaban crystal Modification I obtained has chemical purity of greater than about 99.9% as measured by HPLC and enantiomeric purity of greater than about 99.99% as measured by HPLC; and wherein crystal Modification I of Rivaroxaban obtained is essentially free from other solid state forms of Rivaroxaban.

15. The process of claim 9, wherein the crystal Modification I of Rivaroxaban obtained is characterized by an X-ray powder diffraction pattern having peaks expressed as 2-theta angle positions at about 9.0, 12.0, 14.3, 16.5, 17.4, 18.1, 19.5, 19.9, 21.7, 22.5, 23.4, 24.1, 24.5, 24.7, 25.6, 26.6, 30.1 and 31.8±0.2 degrees substantially in accordance with FIG. 1; and an infra red (FT-IR) spectrum having main bands at about 685, 707, 745, 756, 846, 919, 991, 1010, 1055, 1077, 1120, 1145, 1163, 1285, 1307, 1323, 1340, 1374, 1408, 1429, 1469, 1486, 1517, 1546, 1605, 1647, 1669, 1736, 2867, 2896, 2936, 2976 and 3353 cm$^{-1}$±2 substantially in accordance with FIG. 2.

16. A process for the preparation of Crystal Modification I of Rivaroxaban, comprising:
a) providing a suspension of Rivaroxaban in a solvent medium comprising water and acetone;
b) heating the suspension formed in step-(a) at a temperature of about 50° C. to the reflux temperature of the solvent medium used for sufficient time to obtain Crystal Modification I of Rivaroxaban;
c) cooling the hot suspension to below about 35° C.; and
d) recovering the highly pure crystal Modification I of Rivaroxaban formed in step-(c).

17. The process of claim 16, wherein the amount of solvent medium employed in step-(a) is about 5 volumes to about 40 volumes with respect to the quantity of Rivaroxaban used; wherein the amount of acetone employed in the solvent medium is about 1 to 5 volumes with respect to the volume of water used; wherein the suspension in step-(b) is heated at the reflux temperature of the solvent medium used while stirring; wherein the suspension in step-(c) is cooled at a temperature of about 0° C. to about 30° C.; and wherein the recovering in step-(d) is carried out by the filtration, filtration under vacuum, decantation, centrifugation or a combination thereof.

18. The process of claim 16, wherein the highly pure Rivaroxaban crystal Modification I obtained has chemical purity of greater than about 99.9% as measured by HPLC and enantiomeric purity of greater than about 99.99% as measured by HPLC; and wherein crystal Modification I of Rivaroxaban obtained is essentially free from other solid state forms of Rivaroxaban.

19. The process of claim 16, wherein the crystal Modification I of Rivaroxaban obtained is characterized by an X-ray powder diffraction pattern having peaks expressed as 2-theta angle positions at about 9.0, 12.0, 14.3, 16.5, 17.4, 18.1, 19.5, 19.9, 21.7, 22.5, 23.4, 24.1, 24.5, 24.7, 25.6, 26.6, 30.1 and 31.8±0.2 degrees substantially in accordance with FIG. 1; and an infra red (FT-IR) spectrum having main bands at about 685, 707, 745, 756, 846, 919, 991, 1010, 1055, 1077, 1120, 1145, 1163, 1285, 1307, 1323, 1340, 1374, 1408, 1429, 1469, 1486, 1517, 1546, 1605, 1647, 1669, 1736, 2867, 2896, 2936, 2976 and 3353 cm$^{-1}$±2 substantially in accordance with FIG. 2.

20. Highly pure Rivaroxaban crystal Modification I having chemical purity of greater than about 99.9% as measured by HPLC and enantiomeric purity of greater than about 99.99% as measured by HPLC.

21. The highly pure compound of claim 20, wherein the Rivaroxaban crystal Modification I has a chemical purity of greater than about 99.95% as measured by HPLC.

22. A pharmaceutical composition comprising highly pure Rivaroxaban crystal Modification I, having a chemical purity of greater than about 99.9% as measured by HPLC and an enantiomeric purity of greater than about 99.99% as measured by HPLC, and one or more pharmaceutically acceptable excipients.

23. The pharmaceutical composition of claim 22, wherein the crystal Modification I of Rivaroxaban has a $D_{90}$ particle size of about 1 micron to about 100 microns.

24. The pharmaceutical composition of claim 22, wherein the crystal Modification I of Rivaroxaban is free from other solid state forms.

* * * * *